(12) United States Patent  (10) Patent No.: US 7,445,701 B2
Morioka et al.  (45) Date of Patent: *Nov. 4, 2008

(54) CAPILLARY ARRAY UNIT AND ELECTROPHORESIS BASED THEREON

(75) Inventors: Tomonari Morioka, Hitachinaka (JP); Yasushi Shimizu, Hitachinaka (JP); Seiichi Ugai, Hitachinaka (JP); Toshiaki Kita, Hinode (JP); Kiyoshi Tsukada, Mito (JP)

(73) Assignee: Hitachi Ltd., Tokyo (JP)

( * ) Notice: Subject to any disclaimer, the term of this patent is extended or adjusted under 35 U.S.C. 154(b) by 366 days.

This patent is subject to a terminal disclaimer.

(21) Appl. No.: 11/204,116

(22) Filed: Aug. 16, 2005

(65) Prior Publication Data

US 2006/0049053 A1  Mar. 9, 2006

Related U.S. Application Data (63) Continuation of application No. 10/239,765, filed on Oct. 24, 2002, now Pat. No. 6,977,034.

(51) Int. Cl.
  *G01N 27/453* (2006.01)
(52) U.S. Cl. ...................... 204/603; 204/601
(58) Field of Classification Search ......... 204/600–605, 204/400–405
  See application file for complete search history.

(56) References Cited

U.S. PATENT DOCUMENTS

| 5,228,969 | A | 7/1993 | Hernandez |
| 5,273,633 | A | 12/1993 | Wang |
| 5,324,401 | A | 6/1994 | Yeung et al. |
| 5,582,705 | A | 12/1996 | Yeung et al. |
| 5,790,727 | A | 8/1998 | Dhadwal et al. |
| 5,815,258 | A | 9/1998 | Nakanishi |
| 5,833,827 | A | 11/1998 | Anazawa et al. |
| 5,885,430 | A * | 3/1999 | Kernan et al. ............. 204/453 |
| 5,900,934 | A * | 5/1999 | Gilby et al. ............... 356/344 |
| 6,404,495 | B1 | 6/2002 | Melman et al. |
| 6,977,034 | B2 * | 12/2005 | Morioka et al. ........... 204/603 |

FOREIGN PATENT DOCUMENTS

| GB | 2 314 622 | 7/1998 |
| JP | 5-281134 | 10/1993 |
| JP | 9-96623 | 4/1997 |
| JP | 9-218149 | 8/1997 |
| JP | 10-19845 | 1/1998 |

OTHER PUBLICATIONS

The Quartz Page: Introduction downloaded from www.quartzpage.de/print/intro.html on Oct. 13, 2007.*

* cited by examiner

*Primary Examiner*—Alex Noguerola
(74) *Attorney, Agent, or Firm*—Dickstein Shapiro. LLP (57) ABSTRACT

A capillary array includes multiple capillaries and two holding substrates for arranging the aforementioned multiple capillaries in a substantially plane surface by sandwiching at least some of these capillaries mutually. One of the holding substrates has a detection window for transmitting the detected light emitted by a test sample by irradiation of light. Especially, this detection window includes multiple light transmission areas provided to correspond to each capillary to transmit the detected light, and light cut-off areas provided between these light transmission areas to cut off the detected light. These light cut-off areas cut off light reflected from the surface of capillaries and hence improve the SN ratio, thereby ensuring high-precision detection.

19 Claims, 12 Drawing Sheets

CAPILLARY ARRAY UNIT AND ELECTROPHORESIS BASED THEREON

This application is a continuation of U.S. patent application Ser. No. 10/239,765, filed on Oct. 24, 2002, titled "CAPILLARY ARRAY AND ELECTROPHORESIS APPARATUS," now U.S. Pat. No. 6,977,034, the entire disclosure of which is incorporated herein by reference.

FIELD OF THE INVENTION

The present invention relates to a capillary array electrophoresis apparatus for separating and analyzing such a sample as DNA and protein.

BACKGROUND OF THE INVENTION

Analysis of such a sample as DNA and protein is growing in importance in recent years, and this requires a DNA sequencer to provide a higher speed and greater throughput. One of the examples is found in a capillary array electrophoresis apparatus having multiple capillaries arranged in a plane surface. The capillary array electrophoresis apparatus basically comprises a capillary array, an excitation optical system consisting of a laser light source and the like, and a light receiving optical system fat detecting fluorescent light. The capillary array consists of capillaries arranged on a plane surface.

Laser light is applied to the capillary ifiled with the sample (fluorescent sample) labeled with fluorophore in the direction parallel to the capillary arranged surface, and laser light is condensed by a lens-like function of the capillary, whereby fluorescent samples in all capilliaries are exposed to laser light. The fluorescent sample emits fluorescent light. The light receiving optical system detects the fluorescent light emitted from the fluorescent sample that emits fluorescent light almost normal to the direction of the laser light coming from the laser, thereby measuring the sample.

However, part of the fluorescent light of the fluorescent sample emitted due to application of laser light is reflected by the capillary surface. In the capillary array electrophoresis apparatus disclosed in Japanese Application Patent Laid-Open Publication No. Hei 09-096623, this reflected light is detected by the light receiving optical system to become one of the causes for increase of the background light, resulting in deterioration of the detection accuracy.

To solve this problem, the following configuration is disclosed in the U.S. Pat. No. 5,790,727: Laser light is applied to the capillary filled with fluorescent sample in the direction parallel to the surface where multiple capillaries are arranged. In a capillary array electrophoresis apparatus where a light receiver receives the fluorescent light of the fluorescent sample emitted in the direction normal to laser light, a light extractor consisting of an optical fiber is mounted on the aforementioned capillary in the direction where fluorescent light is detected, in such a way that the light reflected from the capillary surface does not enter the light extractor consisting of an optical fiber. Then the fluorescent light traveling inside the optical fiber is received by the fluorescent light detector, thereby reducing the background light.

According to the prior art disclosed in the aforementioned U.S. Pat. No. 5,790,727, however, an optical fiber is mounted on the fluorescent light detector in order to ensure that the fluorescent light reflected from the capillary surface is not detected by the light receiving optical system, thereby reducing the background light and improving the detection accuracy. While the capillary array is a consumable product, the fluorescent light detector consisting of an optical fiber is a fixture of the apparatus. Accordingly, every time the capillary array is replaced, it is necessary to align the capillary center axis of the capillary array fluorescent light detector and the center axis of the optical fiber constituting the optical extractor. This means a time-consuming work for a user. Further, detection accuracy will deteriorate if misalignment occurs between the center axis of the capillary and that of the optical fiber.

DISCLOSURE OF INVENTION

The object of the present invention is to provide a capillary array characterized by high detection accuracy ensured by reduced background light and improved SN ratio.

Another object of the present invention is to provide a capillary array electrophoresis apparatus characterized by a simplified procedure of mounting the capillary array on the apparatus, high-precision detection and easy use.

The present invention is characterized by comprising multiple capillaries, and a window unit which further comprises first and second holding substrates for arranging the aforementioned multiple capillaries in a substantially plane surface by sandwiching at least some of these capillaries; wherein the aforementioned first holding substrate has a detection window for transmitting the detected light emitted by the test sample in the direction normal to the aforementioned plane surface due to irradiation of light. Especially, the capillary array is configured in such a way that the detection window formed on the first holding substrate comprises multiple light transmission areas provided to correspond to each capillary to transmit the detected light and light cut-off areas provided between the aforementioned light transmission areas to cut off the detected light.

The present invention is further characterized by comprising multiple capillaries, and a window unit further comprising a detection window for transmitting fluorescent light emitted from the sample due to irradiation of the excitation light wherein these capillaries are held so that the capillaries are arranged in a substantially plane surface in a capillary array electrophoresis apparatus for detecting the fluorescent light emitted from the sample by application of excitation light to the aforementioned capillaries. The aforementioned detection window comprises multiple light transmission areas provided to correspond to capillaries to transmit the fluorescent light and multiple light cut-off areas provided adjacent to the aforementioned light transmission.

BEST FORM OF EMBODIMENT OF THE PRESENT INVENTION

The following describes the details of the embodiments according to the present invention with reference to drawings:

Embodiment 1

Figure 1:
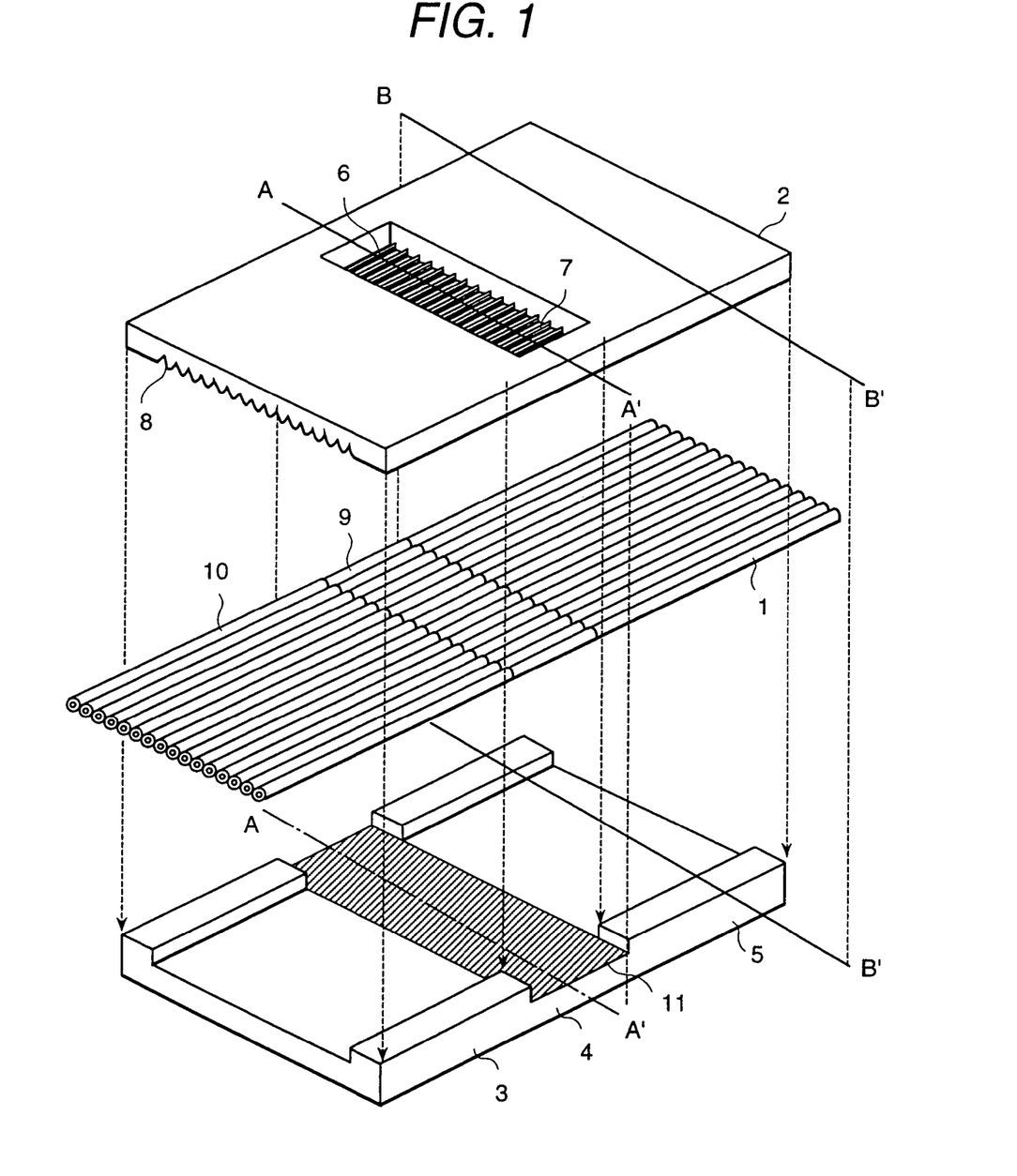
FIG. 1 is a configuration drawing representing the window unit as a first embodiment of the present invention.
Figure 2:
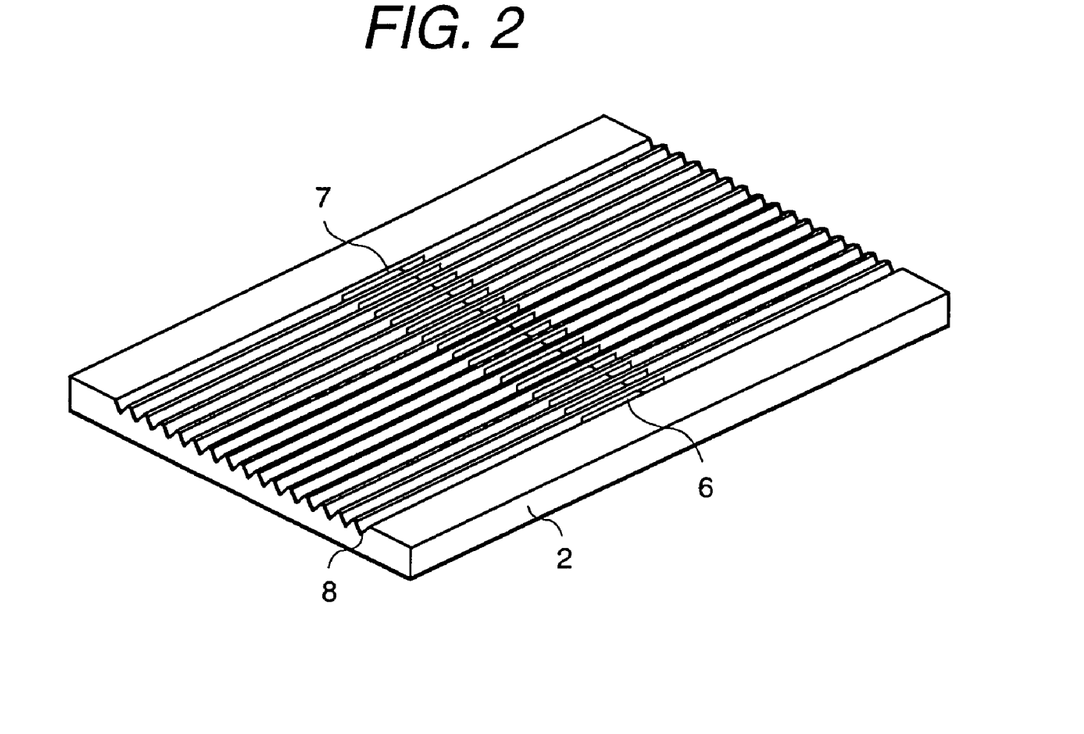
FIG. 2 is an explanatory diagram of the window substrate 2 of FIG. 1 viewed from a different direction.
Figure 3:
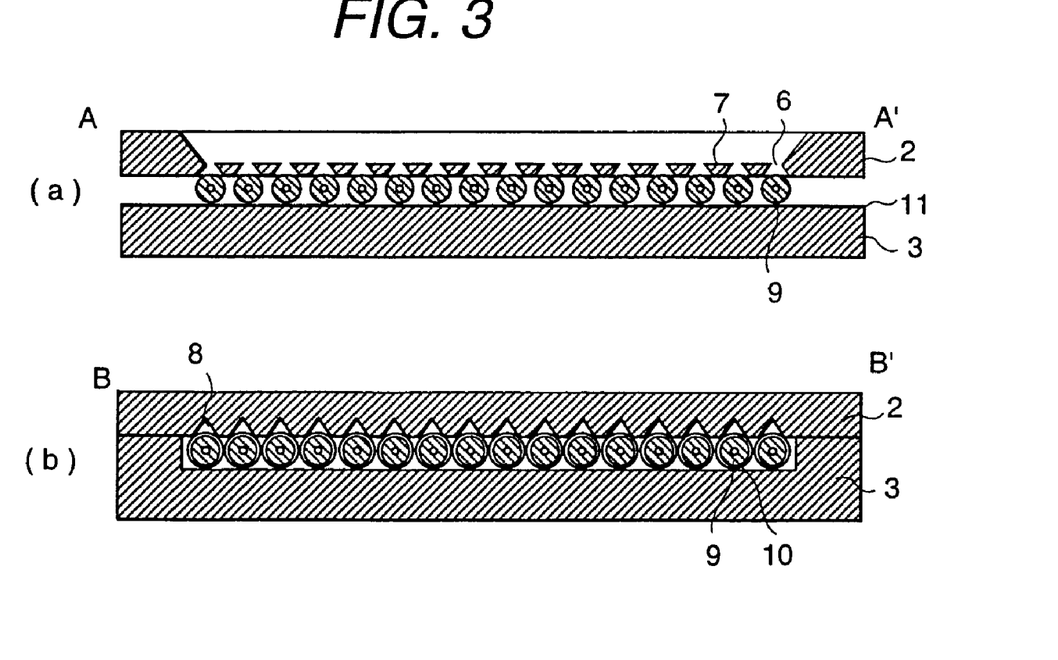
FIG. 3 is cross sectional views taken long lines A-A' and B-B' of the window unit of FIG. 1.

FIG. 1 is a configuration drawing representing the window unit as a first embodiment of the present invention. The window unit comprises a capillary 1, window substrate 2, glass substrate 3, etc. as shown in FIG. 1. FIG. 2 is an explanatory diagram of the window substrate 2 of FIG. 1 viewed from a different direction. FIG. 3 is cross sectional views taken long lines A-A' and B-B' of the window unit of FIG. 1. FIG. 3(a) and FIG. 3(b) correspond to a laser irradiated region 4 and non-irradiated region 5 of FIG. 1, respectively.

As shown in FIG. 1, the window substrate 2 is a silicon substrate. Sixteen openings 6 passed by light are formed in a straight line at the same dimensional interval as that for the arrangement of the capillaries 1, using silicon anisotropic etching technology characterized by excellent processing accuracy. V-grooves 8 having a V-like configuration in cross section are formed on the front and back of the openings 6 corresponding to each of them to position the sequencer of capillaries 1. The light cut-off area 7 partitions sixteen openings 6. These openings and cut-off areas form a detection window. The capillaries 1 are arranged so as to be accommodated in the V-groove 8 of the window substrate 2, and are fixed by adhesive to ensure that the capillaries are sandwiched by a glass substrate 3 from the opposite side. The window unit is formed in this manner. The capillary 1 consists of a molten quartz tube. To increase the bending strength of the capillary 1, the molten quartz tube 9 is covered with a polyimide resin 10. The polyimide resin 10 covering the molten quartz tube 9 is removed for the capillary 1 corresponding to the area forming the opening 6 of the window substrate 2. The portion where the polyimide resin 10 has been removed constitutes a laser irradiated region 4, and the glass substrate 3 of this area has a surface of frosted glass 11, and this reduces the light reflected from the glass substrate 3.

Figure 4:
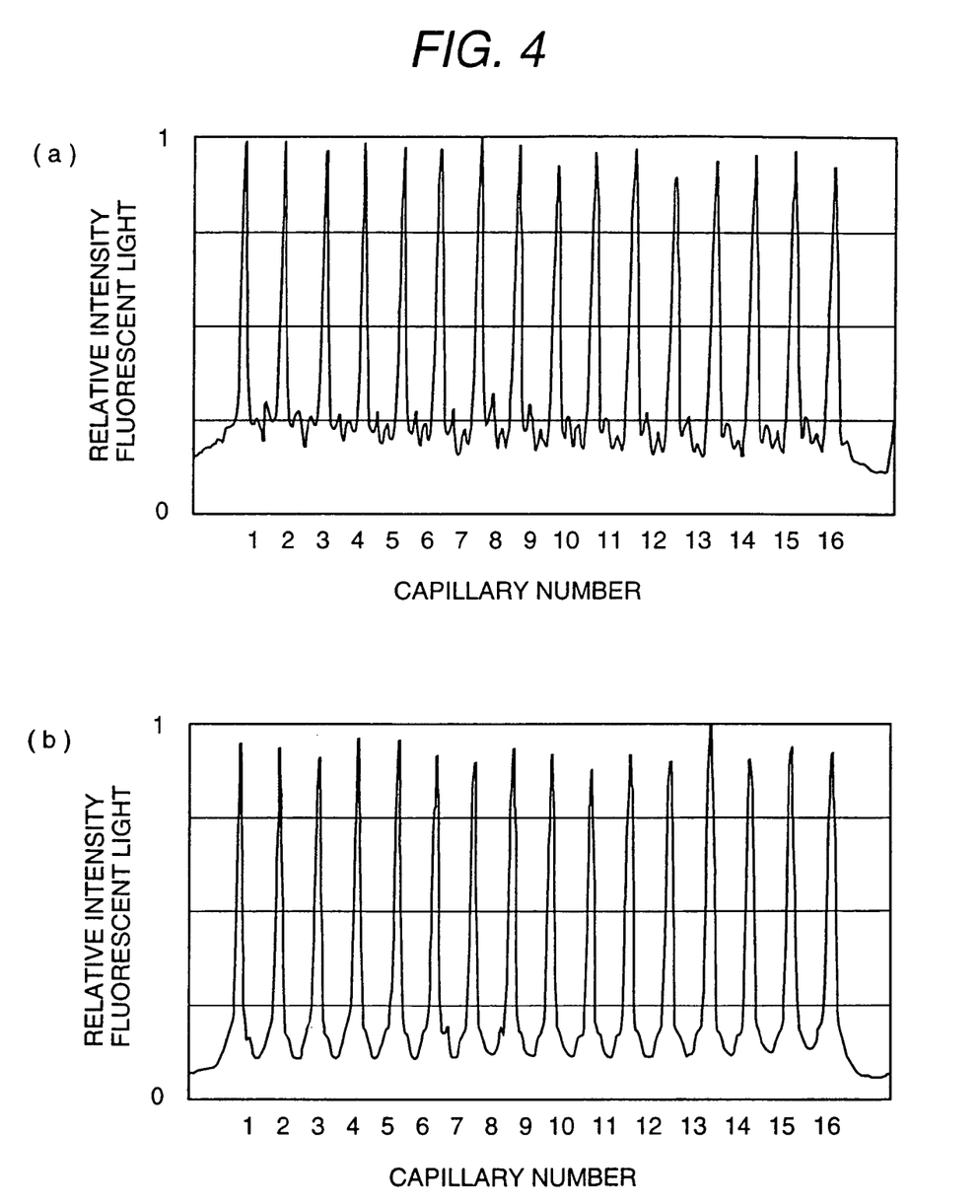
FIG. 4 is an explanatory diagram representing the result of measuring fluorescent light according to the configuration of the first embodiment of the present invention and that of the prior art.

The following describes the result of experiment by comparing between the aforementioned configuration and the prior art configuration disclosed in Japanese Application Patent Laid-Open Publication No. Hei 09-96623. The capillary 1 used in the experiment is made by covering the molten quartz tube 9 having an outer diameter of 0.32 mm and an inner diameter of 0.05 mm with a polyimide resin 10 having a wall thickness of 0.02 mm, and has an outer diameter of 0.36 mm. A urea solution is used as a test sample. Here the urea solution is a substitute for buffer used for electrophoresis. The refractive index of buffer is that same as that of the urea solution. FIG. 4(a) shows the intensity of fluorescent light corresponding to the waveform of 584 nm (fluorescent light by the OH vibration of water due to extension and contraction), based on the prior art configuration disclosed in Japanese Application Patent Laid-Open Publication No. Hei 09-96623 having no window substrate 2. FIG. 4(b) shows the intensity of fluorescent light corresponding to the waveform of 584 nm (fluorescent light by the OH vibration of water due to extension and contraction), based on the window unit having window substrate 2 according to the present invention. The horizontal axis indicates the sequence number of the capillaries 1 arranged in a plane surface, while the vertical axis denotes the relative intensity of fluorescent light standardized at the maximum intensity of fluorescent light. In FIG. 4(a), the intensity of background light is about 20% of the intensity of capillary fluorescent light, and noise is contained among capillaries 1. In the meantime, in FIG. 4(b), a light cut-off area is provided to cut off the light reflected from the surface of the capillary 1. This makes it possible to reduce down to about 10 percent of the intensity of capillary fluorescent light. Further, the noise among capillaries 1 can also be reduced. This improves the SN ratio and allows detection of the signal whose intensity of fluorescent light is smaller.

As shown in FIG. 1, the capillary 1 has polyimide resin 10 removed from the area forming the opening 6 on the window substrate 2, but such a place is not restricted to this area alone. Further, the coating material of the capillary 1 is not limited to polyimide resin 10. It is possible to use other members having the same level of electric insulation and other properties as those of the polyimide resin 10. The window substrate is not restricted to a silicon substrate alone. The same effects as those of the aforementioned embodiment can be obtained from the use of a metal, ceramic or resin.

Embodiment 2

Figure 5:
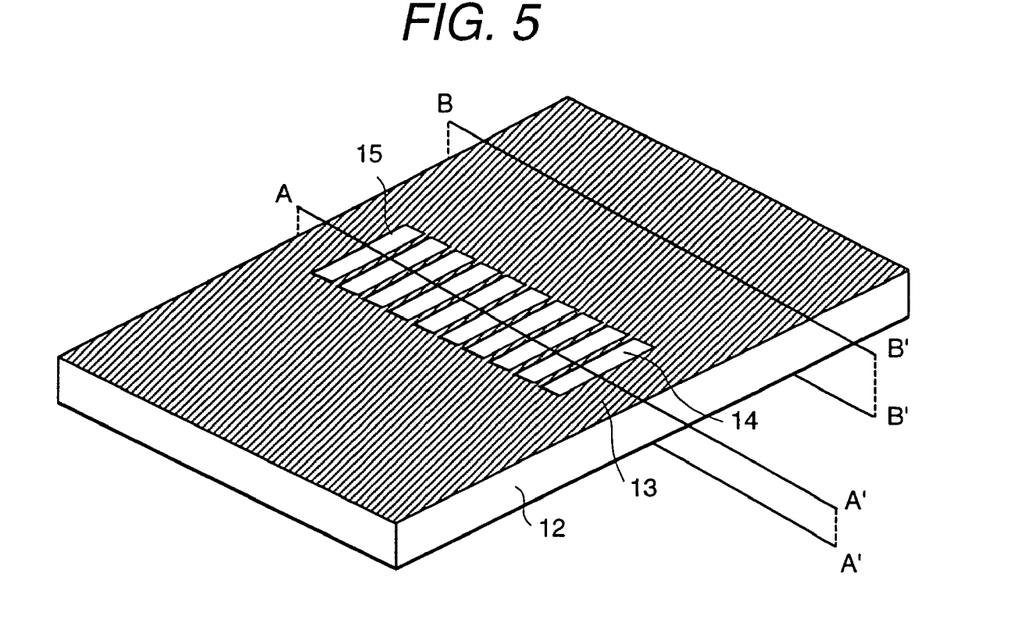
FIG. 5 is a configuration drawing representing the window unit as a second embodiment of the present invention.

FIG. 5 is a configuration drawing representing the window unit as a second embodiment of the present invention. Its difference from the first embodiment is that a transparent substrate 12 such as a glass substrate for transmitting light is used as a window substrate, and the low light-transmittance member 13 is created, for example, by vapor deposition. The first embodiment is configured to have an opening 6, but the present embodiment uses a non-penetration window 14. This non-penetration window 14 is formed by removing the low light-transmittance member 13 by etching to ensure that it is formed at the same interval as that of the arranged capillaries 1. A non-penetration window frame formed cut-off area 15 partitions this non-penetration window 14, thereby reducing transmission of light through the non-penetration window frame formed cut-off area 15, and minimizing the background light. In the window unit as the second embodiment, almost the same effects as those in the embodiment 1 can be obtained.

Figure 6:
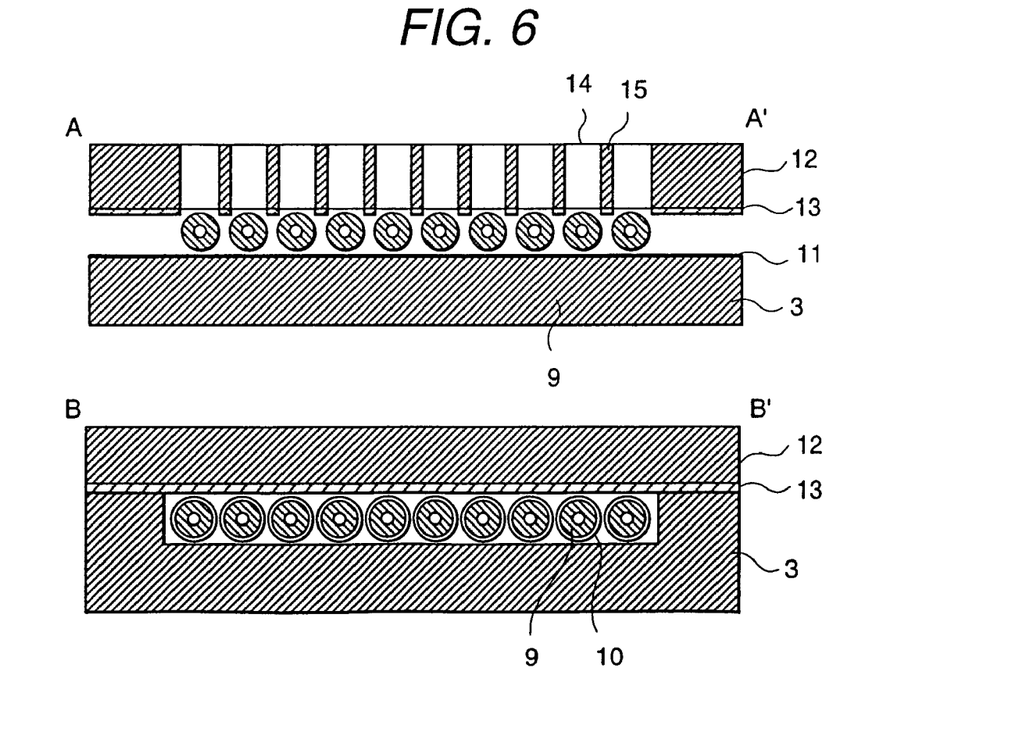
FIG. 6 is cross sectional views taken long lines A-A' and B-B' of the window unit when a substrate 12 of FIG. 5 is used.

Instead of vapor deposition method, printing method can be used to form the low light-transmittance member 13. Further, the low light-transmittance member 13 can be bonded. It is also possible to reverse the order of forming the non-penetration window 14 and low light-transmittance member 13. In FIG. 5, the non-penetration window 14 is formed in a rectangular form, but need not be rectangular. FIG. 6 is cross sectional views taken long lines A-A' and B-B' of the window unit when a substrate 12 of FIG. 5 is used. FIG. 6(a) corresponds to the laser beam irradiated region and FIG. 6(b) the non-irradiated region.

Embodiment 3

Figure 7:
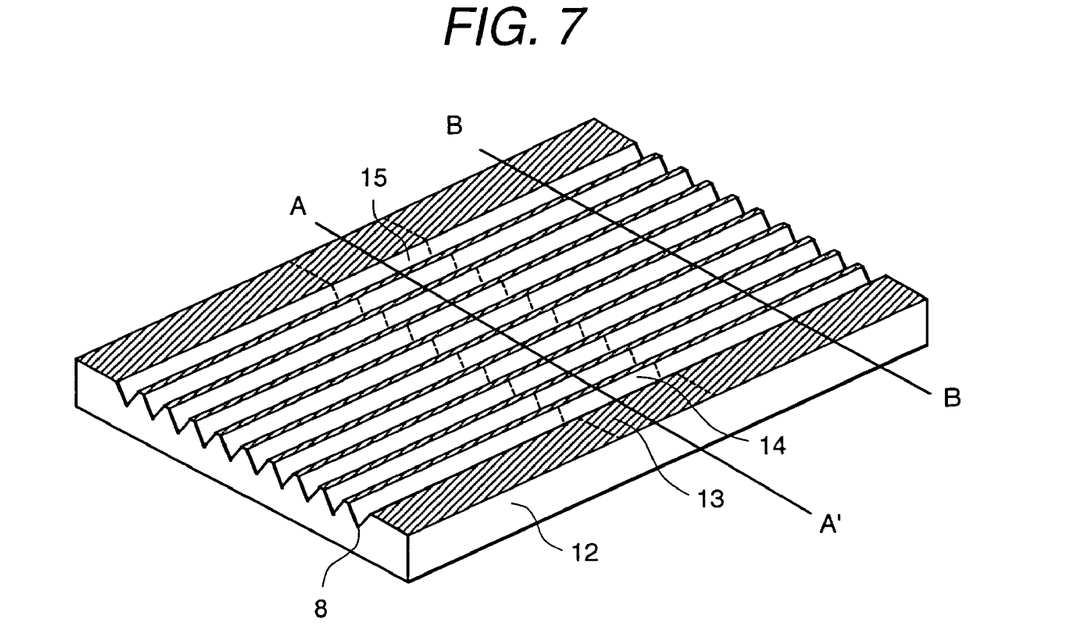
FIG. 7 is a configuration drawing representing the window unit as a third embodiment of the present invention.

FIG. 7 is a configuration drawing representing the window unit as a third embodiment of the present invention. The difference from the aforementioned embodiment 2 is that non-penetration windows 14 are formed on the transparent substrate 12 such as a glass substrate for transmitting light as window substrate, and V-grooves 8 having a V-like configuration in cross section are formed on the front and back of the non-penetration window 14 in order to position the capillary 1 sequence. In the window unit as the third embodiment, the same effects as those of the second embodiment can be obtained. Further, V-grooves 8 are provided to position the sequence of capillaries 1, thereby reducing the misalignment of the capillaries and improving the workability.

Figure 8:
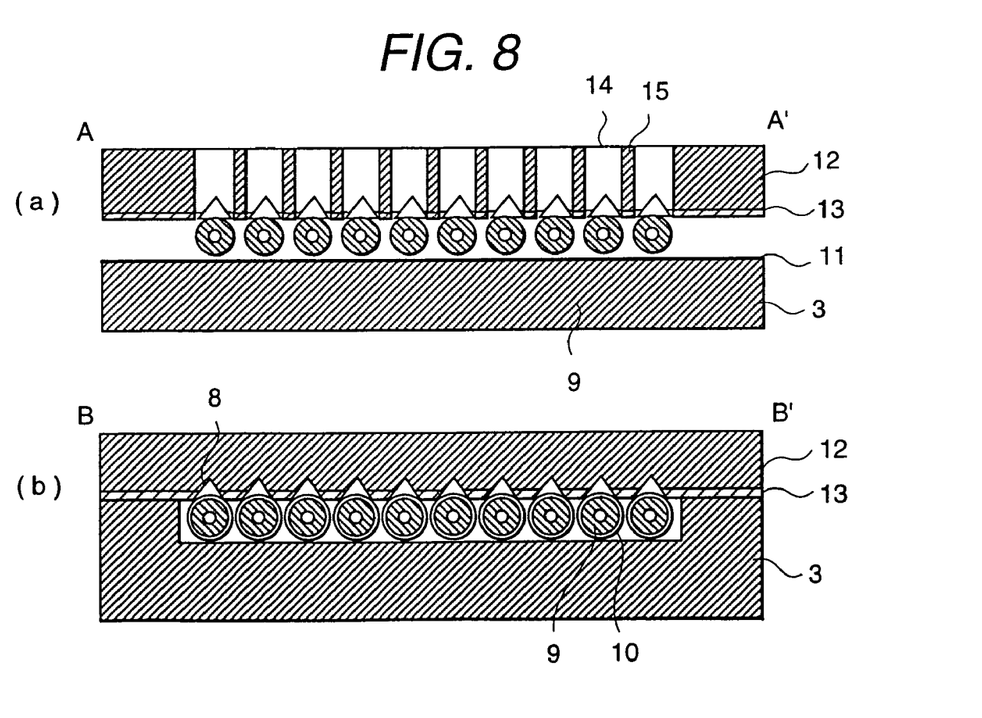
FIG. 8 is cross sectional views taken long lines A-A' and B-B' of the window unit when a substrate 12 of FIG. 7 is used.

FIG. 7 shows the non-penetration window 14 configured in a rectangular form, but the form is not restricted to a rectangular one. The number of non-penetration windows 14 is not limited to ten. The same openings 6 as those of the embodiment can be used by making the non-penetration window 14 into a light penetrating one. FIG. 8 is cross sectional views taken long lines A-A' and B-B' of the window unit when a substrate 12 of FIG. 7 is used. FIG. 8(a) corresponds to the laser beam irradiated region and FIG. 8(b) the non-irradiated region.

Embodiment 4

Figure 9:
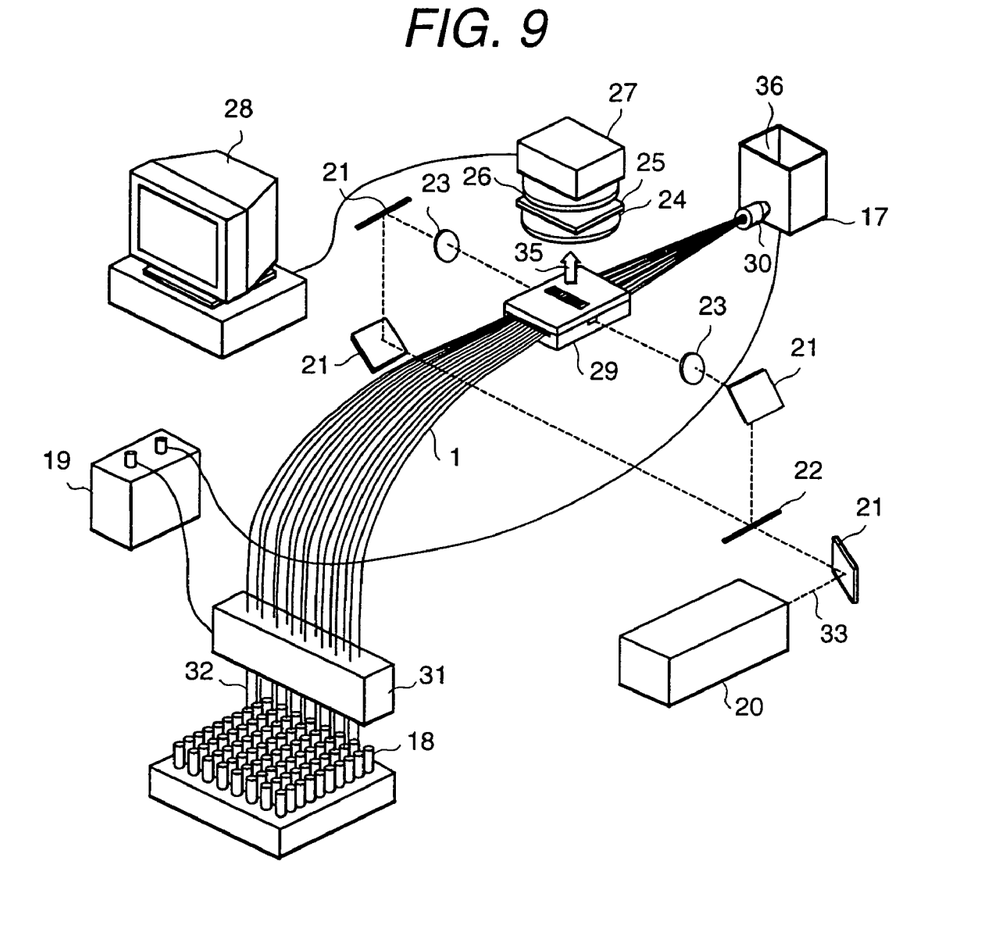
FIG. 9 is an overall configuration view of a capillary array electrophoresis apparatus using the window unit explained with reference to the aforementioned first to third embodiments.
Figure 10:
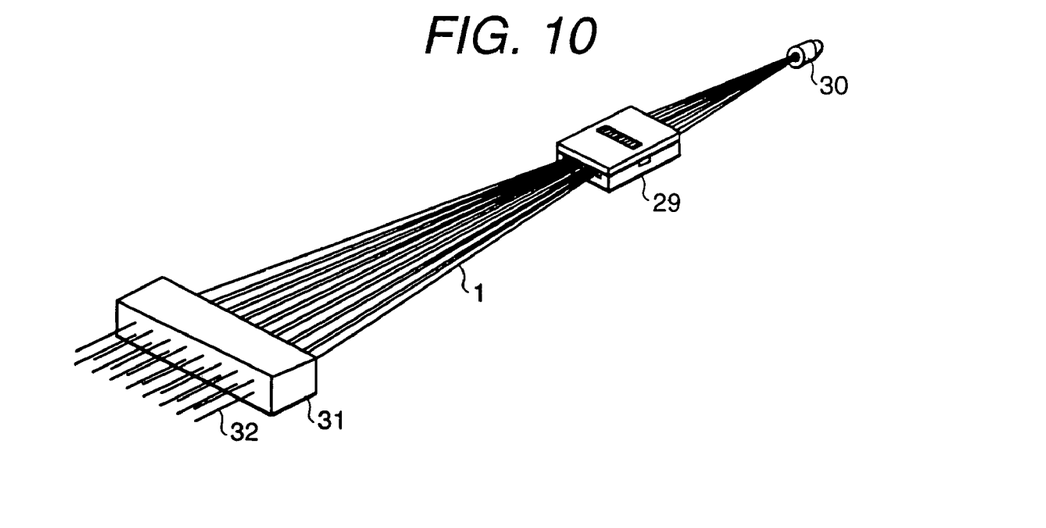
FIG. 10 is a configuration view of a capillary array unit as a sample measuring component of the capillary array electrophoresis apparatus shown in FIG. 9.

FIG. 9 is an overall configuration view of a capillary array electrophoresis apparatus using the window unit explained with reference to the aforementioned first to third embodiments. FIG. 10 is a configuration view of a capillary array unit as a sample measuring component of the capillary array electrophoresis apparatus shown in FIG. 9. As shown in FIG. 9, the capillary array electrophoresis apparatus comprises a capillary array unit, buffer vessel 17, fluorescent sample vessel 18, high voltage power source 19, laser light source 20, mirror 21, beam splitter 22, condensing lens 23, first lens 24, optical filter, image splitting prism 25, second lens 26, CCD camera 27, processor 28, etc. The capillary array unit comprises a capillary 1, window unit 29, buffer inlet 30, electrode plate with protective cover 31, conductive fluorescent sample inlet 32, etc., as shown in FIG. 10. The window unit described in the first to third embodiments is used as window unit 29.

The following describes the operating principle: as shown in FIG. 9, laser light 33 emitted from the laser light source 20 is divided into two by a beam splitter 22, and the traveling direction is changed by a mirror 21. The laser light 33 is condensed by a condensing lens 23, and is applied to the capillaries 1 in the direction parallel to the plane surface where the capillaries 1 are arranged. The capillaries 1 are filled with fluorophore labeled samples (fluorescent samples 34), and the fluorescent samples 34 emit fluorescent light when laser light 33 is applied to the fluorescent samples 34. The fluorescent light 35 is detected as follows: The fluorescent light emitted in the direction almost normal to the plane surface where capillaries 1 are arranged is formed into a parallel light by means of a first lens 24, and the image is split by the optical filter and image splitting prism 25. After that, the image is formed on a CCD camera 27 by a second lens 26. Thus, the fluorescent light 35 is detected by this CCD camera 27. The measurement data having been detected is processed by the processor 28.

In FIG. 9, laser light 33 is irradiated from both sides of the window unit 29, but it is also possible to make it to be irradiated from only one side. Further, laser light 33 can be irradiated in the direction almost normal to the surface where capillaries are arranged, namely, in the direction almost normal to the inspection window of the window unit 29, instead of from the side of the window unit (parallel to the surface where capillaries are arranged). The configuration of the light receiving optical system is not restricted to the one shown in FIG. 9. For example, grating (diffraction grating) can be used instead of the image splitting prism 25. Further, the number of the capillaries 1 of the capillary array unit is not limited to 16. The configuration of the buffer inlet 30 and conductive fluorescent sample inlet 32 is not restricted to the one shown in FIG. 9.

The following describes the operation procedure of the capillary array electrophoresis apparatus. The buffer 36 in the buffer vessel 17 is poured into the capillaries 1 from the buffer inlet 30 of the window unit 16. Then the conductive fluorescent sample inlet 32 is placed into the fluorescent sample vessel 18 filled with fluorescent samples, and fluorescent samples are poured into the capillaries 1. After that, the conductive fluorescent sample inlet 32 is placed into the buffer vessel (not illustrated) filled with buffer, and high voltage is applied to the area between the buffer inlet 30 and conductive fluorescent sample inlet 32 from the high voltage power source 19, whereby electrophoresis is performed. The migrating speed in electrophoresis is proportional to the size of electric charge, and is inversely proportional to the size of molecule, so the fluorescent sample 34 is separated. Electrophoresis is caused to take place for a long time by a long application of high voltage. Fluorescent light 35 emitted at this time is measured on a continuous basis.

When the window unit 29 is provided with the light cut off area 7 and non-penetration window frame formed cut-off area 15, light reflected from the surface of capillary 1 is cut off; therefore, background light is reduced and the SN ratio is improved. This makes it possible to detect signals with smaller intensity of fluorescent light and ensures high precision measurement.

Embodiment 5

Figure 11:
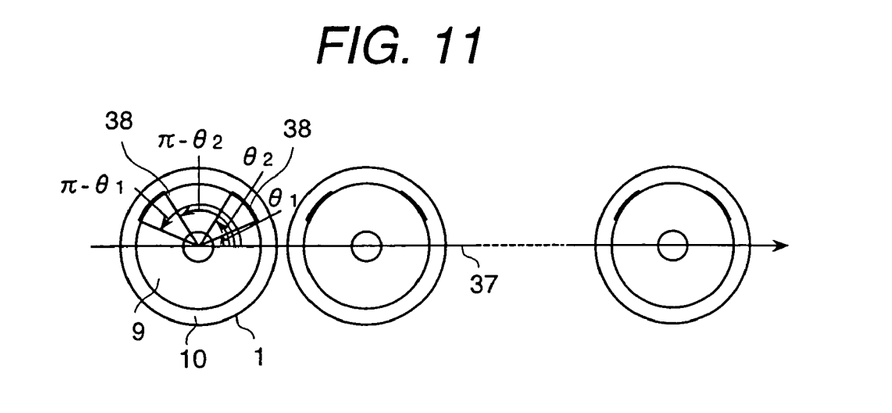
FIG. 11 is a cross sectional view of the capillary having a light cut-off film as a fifth embodiment of the present invention.

FIG. 11 is a cross sectional view of the capillary having a light cut-off film as a fifth embodiment of the present invention. In the first to third embodiments, the window unit 29 is provided with the light cut off area 7 and non-penetration window frame formed cut-off area 15. The difference is that the capillary itself is equipped with the light cut-off film in the present embodiment. The following describes the present embodiment. The capillaries 1 are arranged on a plane surface. Assume that the capillary sequence axis 37 running through the capillary center in the direction where capillaries 1 are arranged is a coordinate axis, and the capillary center axis is a rotary center axis. Then a capillary light cut-off film 38 is formed within the following ranges of capillaries 1:

$$\theta 1 < X < \theta 2$$

$$\pi - \theta 2 < X < \pi - \theta 1$$

where $0 < \theta 1 < \theta 2 < \pi/2$

Figure 12:
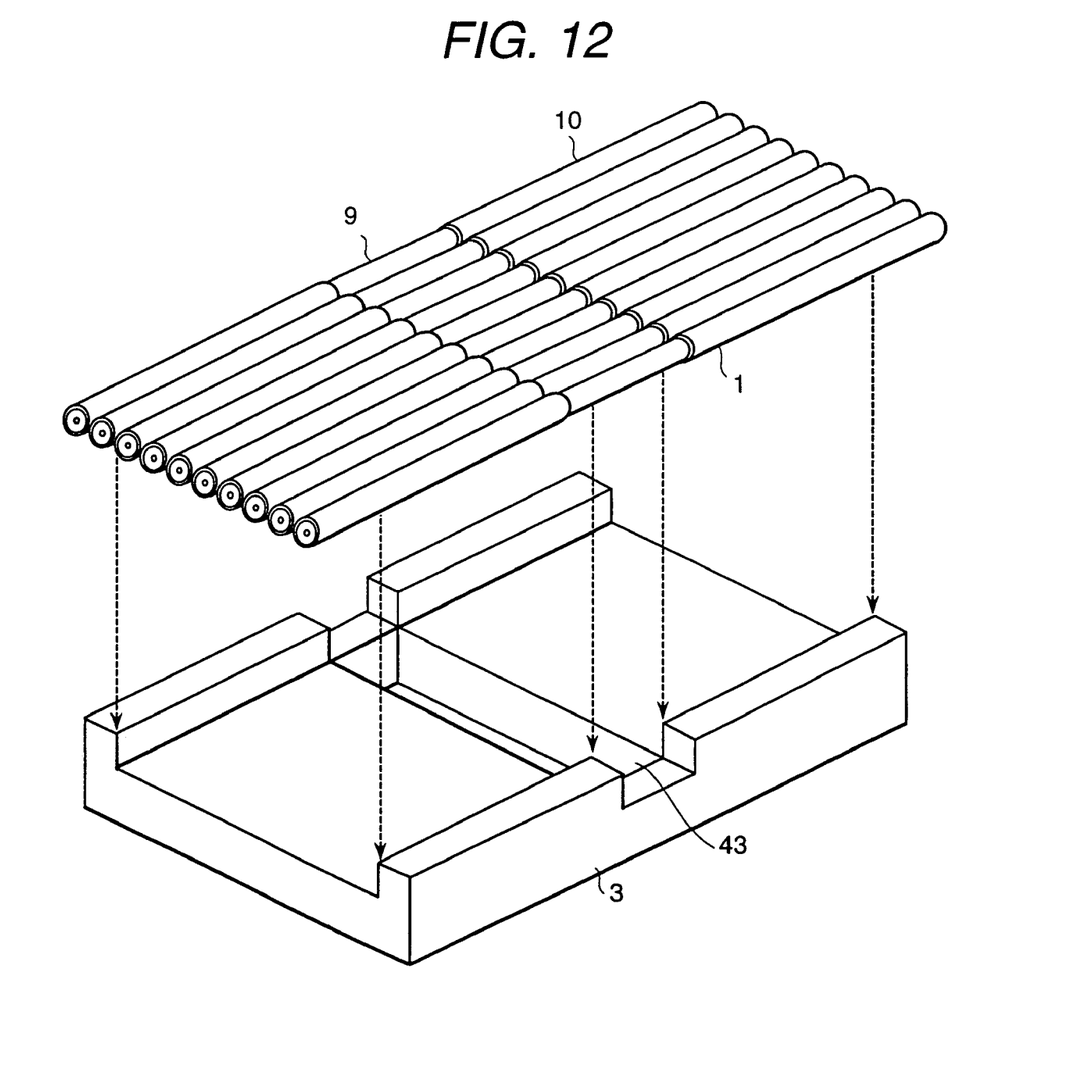
FIG. 12 is a drawing representing an example of the process for forming a capillary comprising the light cut-off film shown in FIG. 11.
Figure 13:
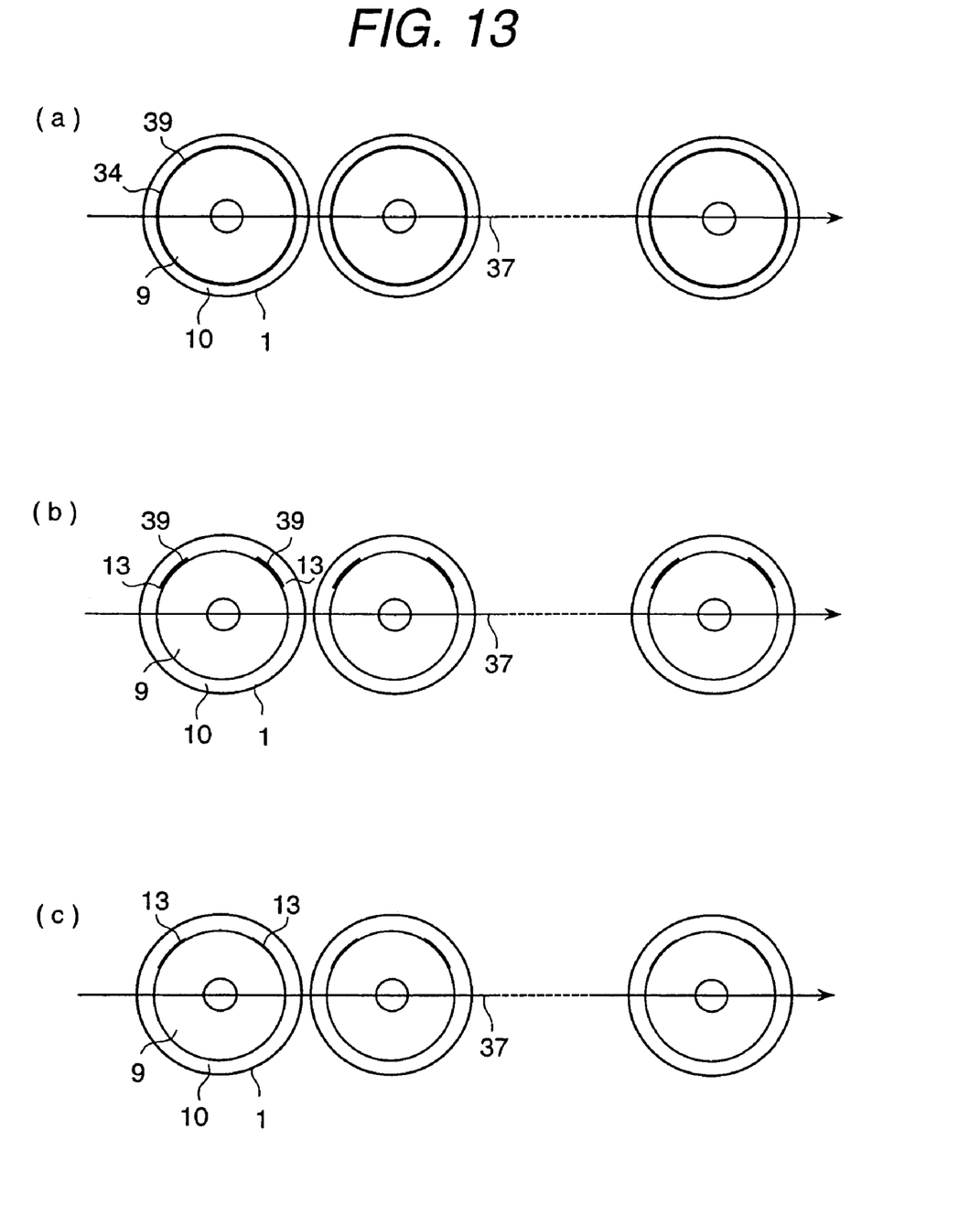
FIG. 13 is a drawing representing an example of the process for forming a capillary comprising the light cut-off film shown in FIG. 11.

With reference to FIGS. 12 and 13, the following describes an example of the process for forming a capillary comprising the light cut-off film shown in FIG. 11. As shown in FIG. 13(*a*), a low light-transmittance member 13 is formed by vapor deposition on the portion of the capillary 1 where the polyimide resin 10 has been removed. Then resist 39 is applied thereon. After that, capillaries 1 coated with the resist are arranged on the glass substrate 3, as shown in FIG. 12. In this case, they are arranged in such a way that the portions of the capillaries 1 where the polyimide resin 10 has been removed can be associated with through-holes 43 formed on the glass substrate 3. Then development is made after the resist 39 is exposed to light by exposure and low light-transmittance member 13 is removed by etching, as shown in FIG. 13(*b*). Lastly, the resist 39 remaining on the capillaries 1 is removed, as shown in FIG. 13(*c*). In this fifth embodiment, the same effects as those of the first embodiment can be obtained. It should be noted that the method of forming the low light-transmittance member 13 is not restricted to the aforementioned one. It can be formed by printing technique or the like.

Embodiment 6

Figure 14:
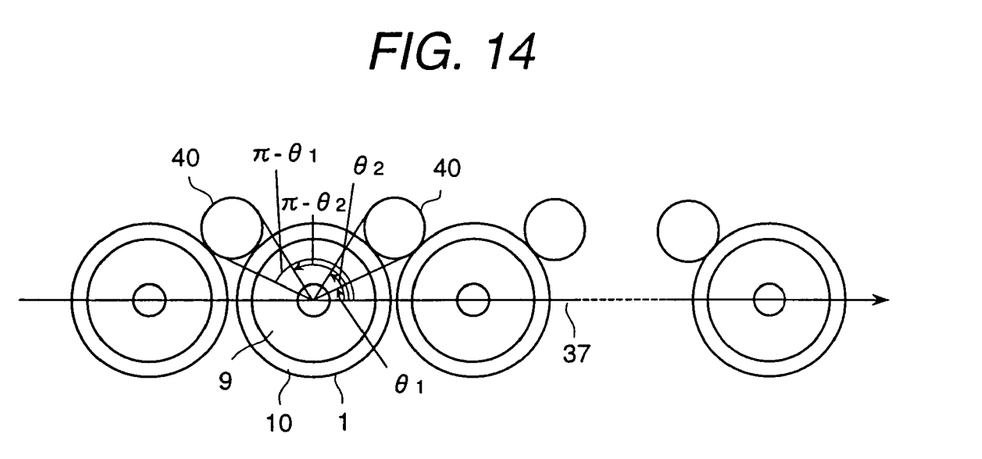
FIG. 14 is a cross sectional view of a capillary fluorescent light detector as an sixth embodiment of the present invention.

FIG. 14 is a cross sectional view of a capillary fluorescent light detector as a sixth embodiment of the present invention. In the present embodiment, a capillary light cut-off rod 40 consisting of a low light-transmittance member 13, instead of the capillary light cut-off film 38 used in the embodiment 5, is bonded on the outer periphery of the capillary 1 within the following range:

$$\theta 1 < X < \theta 2$$

$$\pi - \theta 2 < X < \pi - \theta 1$$

where $0 < \theta 1 < \theta 2 < \pi/2$

The same effects as those of embodiment 1 can be from the configuration of the capillary fluorescent light detector as the sixth embodiment.

Embodiment 7

Figure 15:
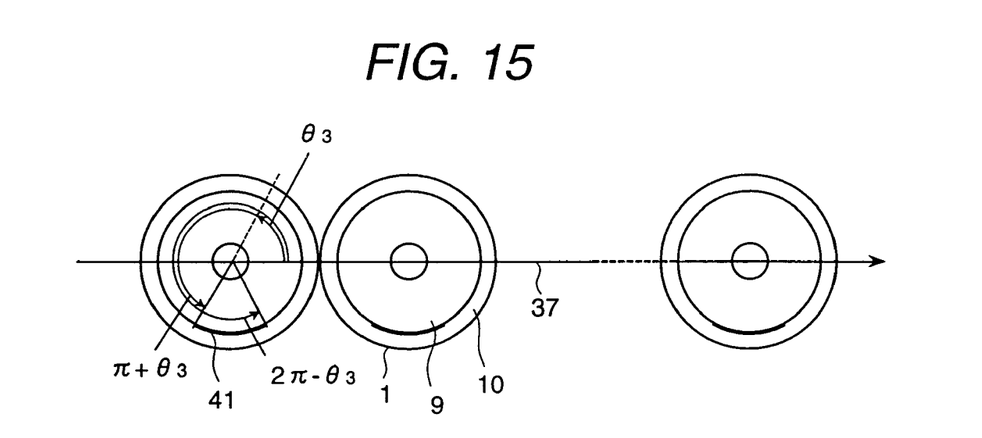
FIG. 15 is a cross sectional view of a capillary having a reflection film as a seventh embodiment of the present invention.

FIG. 15 is a cross sectional view of a capillary having a reflection film as a seventh embodiment of the present invention. The capillaries 1 are arranged on a plane surface. Assume that the capillary sequence axis 37 running through the capillary center in the direction where capillaries 1 are arranged is a coordinate axis, and the capillary center axis is a rotary center axis. Then a capillary light reflecting film 41 is formed within the following ranges of capillaries 1:

$$\pi + \theta 3 < X < 2\pi - \theta 3$$

where $0 < \theta 3 < \pi/2$

Here the reflection factor of the capillary light reflecting film 41 is assumed as greater that of the capillary.

Figure 16:
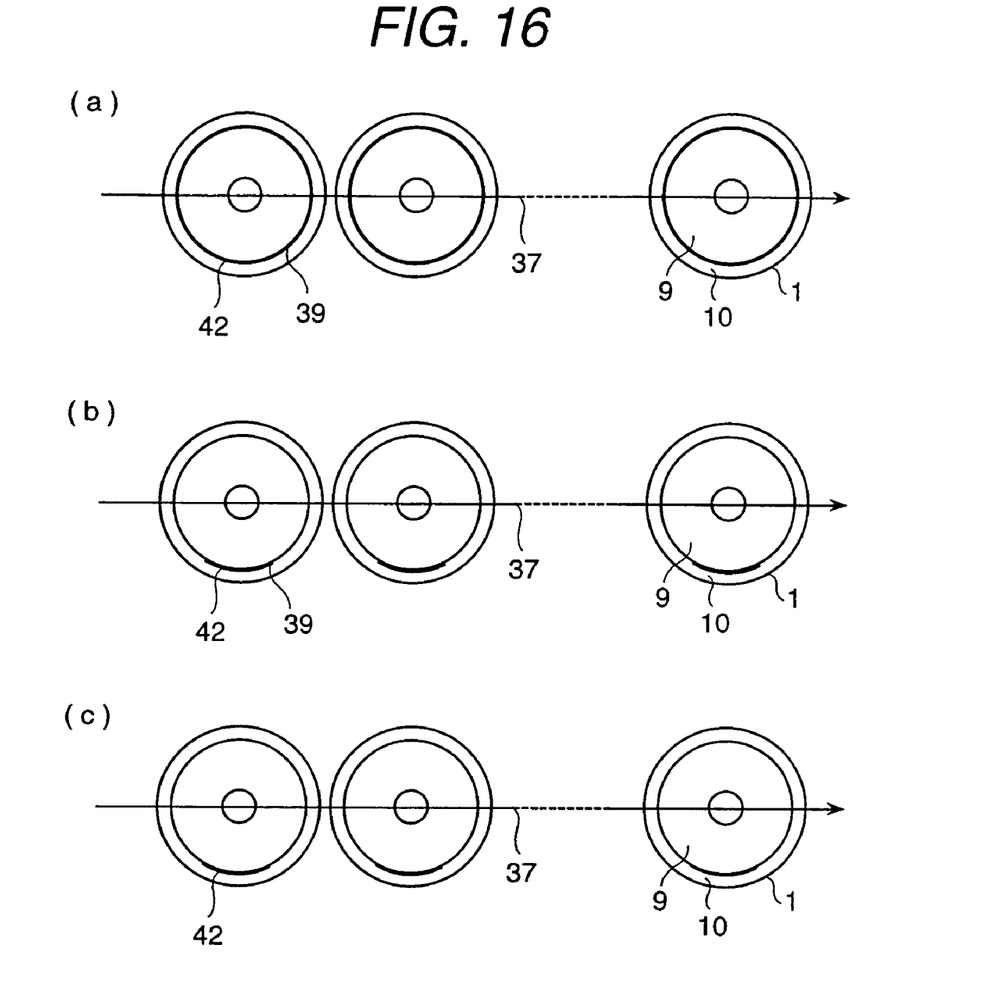
FIG. 16 is an explanatory diagram showing a process of forming a capillary comprising the light reflection film shown in FIG. 15.

FIG. 16 shows an example of the process of forming a capillary comprising the reflection film shown in FIG. 15. As shown in FIG. 16(*a*), a high reflection factor member 42 is formed by vapor deposition on the portion where the polyimide resin 10 of the capillary 1 has been removed, and resist 39 is applied thereon. After that, capillaries 1 coated with the resist are arranged on the glass substrate 3, as shown in FIG. 12. Then development is made after the resist 39 is exposed to light by exposure and high reflection factor member 42 is removed by etching, as shown in FIG. 16(*b*). Lastly, the resist 39 remaining on the capillaries 1 is removed, as shown in FIG. 16(*c*).

According to the capillary comprising a light reflecting film as the seventh embodiment, fluorescent light 35 reflected from the surface of the capillary reflecting film 41 is also detected. This increases the intensity of capillary fluorescent light and hence improves the SN ratio substantially, with the result that high precision detection can be ensured. It should be noted that the method of forming the high reflection factor member 42 is not restricted to the aforementioned one. It can be formed by printing technique or the like.

Embodiment 8

Figure 17:
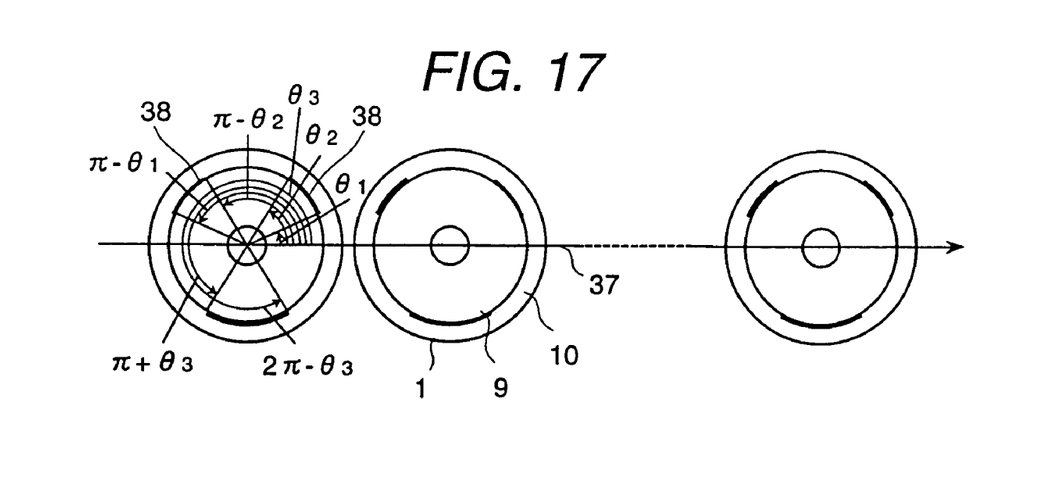
FIG. 17 is a cross sectional view of a capillary having a light cut-off film and reflection film as an eighth embodiment of the present invention.

FIG. 17 is a cross sectional view of a capillary having a light cut-off film and reflection film as an eighth embodiment of the present invention. The capillaries 1 are arranged on a plane surface. Assume that the capillary sequence axis 37 running through the capillary center in the direction where capillaries 1 are arranged is a coordinate axis, and the capillary center axis is a rotary center axis. Then a capillary light cut-off film 38 is formed within the following ranges of capillaries 1:

$$\theta 1 < X < \theta 2$$

$$\pi - \theta 2 < X < \pi - \theta 1$$

where $0 < \theta 1 < \theta 2 < \pi/2$

Further, a capillary light reflecting film is also formed within the following ranges of capillaries 1:

$$\pi + \theta 3 < X < 2\pi - \theta 3$$

where $0 < \theta 3 < \pi/2$

Here the reflection factor of the capillary light reflecting film 41 is assumed as greater that of the capillary.

Figure 18:
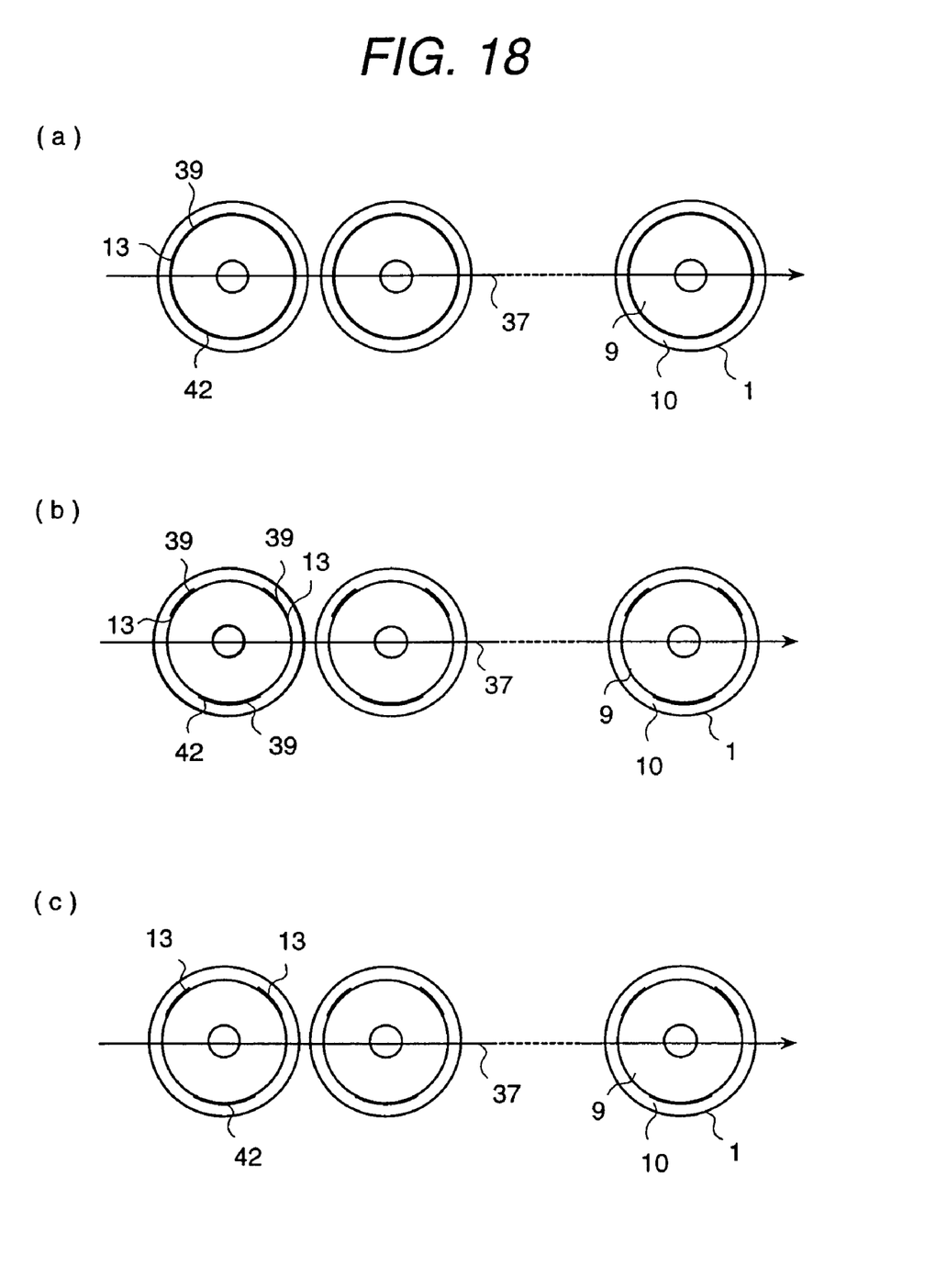
FIG. 18 is an explanatory diagram showing a process of forming a capillary comprising a light cut- off film and a reflection film.

FIG. 18 shows an example of the process of forming a capillary comprising a light cut-off film and a reflection film. Capillaries 1 are arranged on the glass substrate 3 as shown in FIG. 12. A low light-transmittance member 13 is formed by vapor deposition on one side of the portion where the polyimide resin 10 has been removed, and a high reflection factor member 42 on the other side, as shown in FIG. 18(*a*). The resist 39 is applied thereon. After that, development is made after the resist 39 is exposed to light by exposure, as shown in FIG. 18(*b*) and the low light-transmittance member 13 and high reflection factor member 42 are removed by etching. Lastly, the resist 39 remaining on the capillaries 1 is removed, as shown in FIG. 18(*c*). The same effects as those of the first embodiment can be obtained by using the capillary comprising a light cut-off film and reflective film as the eighth embodiment. Further, the capillary reflecting film 41 formed on the capillary 1 increases the intensity of capillary fluorescent light and hence improves the SN ratio, with the result that high precision detection is ensured. It should be noted that the method of forming the low light-transmittance member and high reflection factor member 42 is not restricted to the aforementioned one. It can be formed by printing technique or the like.

Figure 19:
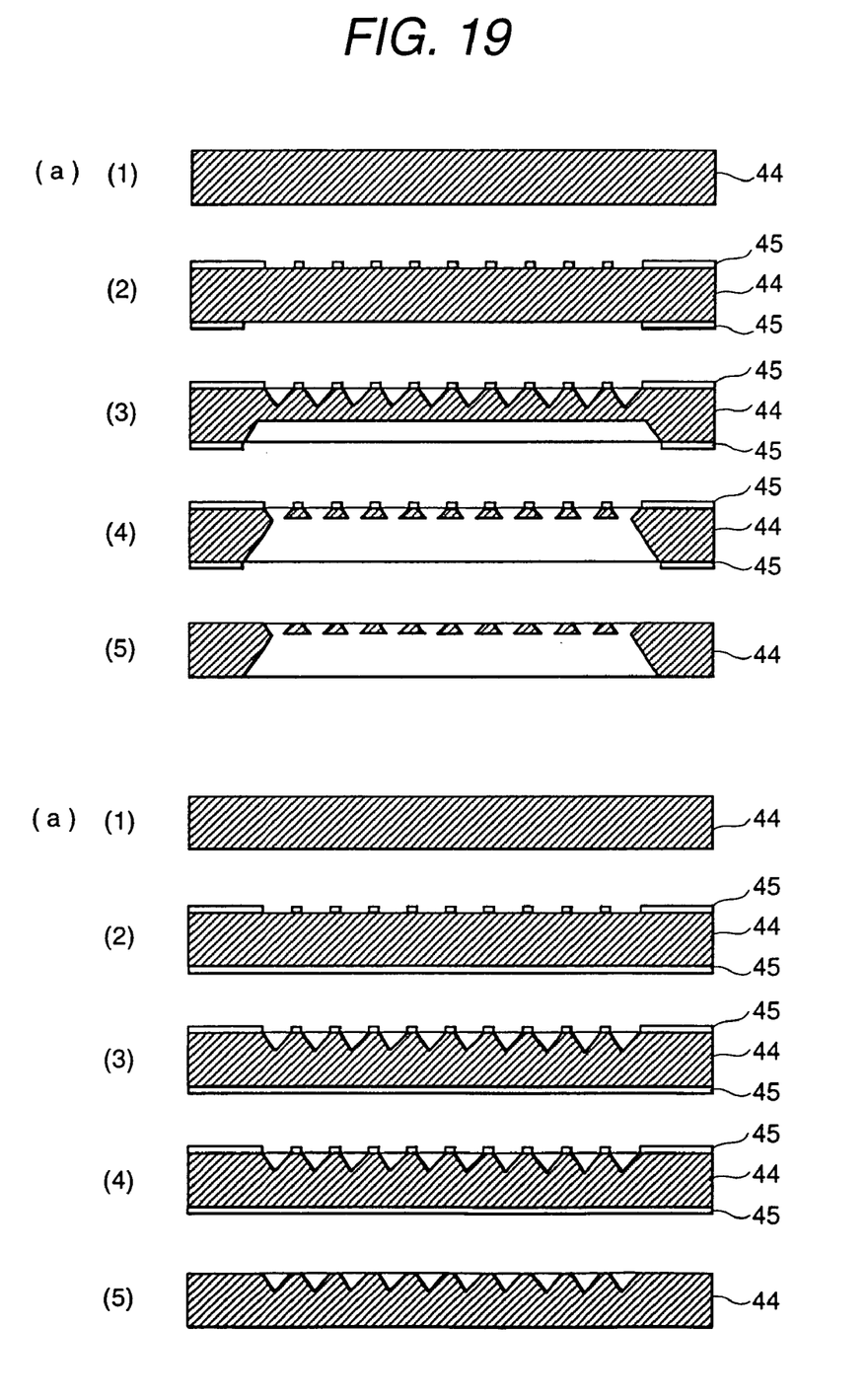
FIG. 19 is an explanatory diagram showing a method of forming a silicon substrate 2 used as a window substrate in the first embodiment of the present invention.

FIG. 19 is an explanatory diagram showing the method of forming a silicon substrate 2 used as a window substrate in the first embodiment of the present invention. FIGS. 19(a) and 19(b) correspond to the laser irradiated region 4 and non-irradiated region 5, respectively. The following describes the method for formation with reference to FIG. 19. As shown in FIG. 19(a) <1>, a thermally grown oxide film 44 is formed on the surface of the silicon substrate 2, and resist 39 is applied thereon. Then development and exposure are made, and the oxide film is etched with HF solution. After that, silicon anisotropic etching is provided as shown in FIG. 19(a) <3> to <4>. Lastly, the resist 45 and oxide film are removed, as shown in FIG. 19(a) <5>. The process shown in FIG. 19(b) is the same as the one described with reference to the aforementioned FIG. 19(a), and will not be described here to avoid duplication. In this way, use of silicon anisotropic etching characterized by excellent processability ensures mass production of substrates at fewer costs. It should be noted that openings 6 and V-grooves 8 having a V-like configuration in cross section are formed in FIG. 19, but V-grooves 8 need not necessarily be formed. Only the openings 6 are sufficient for the purpose. Further, the etching mask agent is not restricted to thermally grown oxide film. Silicon etching method is not limited to KOH wet etching. The profile of the silicon to be processed is not restricted to the processing method shown in FIG. 19 since it varies according to the thickness of the silicon and profile of the mask.

As described above, in a capillary array electrophoresis apparatus according to the present invention, the window unit as a capillary array holding substrate comprises openings for transmitting detected light, and a light cut-off area for cutting off light reflected from the capillary surface. This configuration reduces the background light and hence improves the SN ratio, thereby ensuring high-precision detection.

What is claimed is:

1. An electrophoresis apparatus comprising:
multiple capillaries to allow migration of test samples, said capillaries being arranged substantially in a plane and having an area to which an excitation light is irradiated;
a holding member for arranging at least some of said capillaries including said area substantially in said plane;
a light exciting system for irradiating said excitation light to said capillaries;
a light receiving optical system for detecting a fluorescent light from said migration of said test samples; and
a light cut-off means arranged on said capillaries, said light cut-off means being arranged to cut off light exiting said capillaries and comprising a curved surface.

2. An electrophoresis apparatus of claim 1, wherein a portion of said holding member is configured for reducing reflected light.

3. An electrophoresis apparatus of claim 1, wherein said holding member comprises a glass substrate, and wherein part of a surface of said glass substrate is frosted.

4. An electrophoresis apparatus comprising:
multiple capillaries to allow migration of test samples, said capillaries being arranged substantially in a plane and having an area to which an excitation light is irradiated;
a holding member for arranging at least some of said capillaries including said area substantially in said plane;
a light exciting system for irradiating said excitation light to said capillaries;
a light receiving optical system for detecting a fluorescent light from said migration of said test samples; and
a light cut-off means arranged on said capillaries, said light cut-off means being arranged to cut off light exiting said capillaries and comprising a curved surface, wherein said light cut-off means comprises a light cut-off film arranged on said capillaries to either side of an axis in a direction of light emitted from said area to which an excitation light is irradiated and detected by said light receiving optical system.

5. An electrophoresis apparatus comprising:
multiple capillaries to allow migration of test samples, said capillaries being arranged substantially in a plane and having an area to which an excitation light is irradiated;
a holding member for arranging at least some of said capillaries including said area substantially in said plane;
a light exciting system for irradiating said excitation light to said capillaries;
a light receiving optical system for detecting a fluorescent light from said migration of said test samples; and
a light cut-off means arranged on said capillaries, said light cut-off means being arranged to cut off light exiting said capillaries and comprising a curved surface, wherein said multiple capillaries include capillaries comprising a cylindrical molten quartz tube and a polyimide resin covering a portion of said molten quartz tube, and wherein said light cut-off means is arranged on a portion of the molten quartz tube not covered by said polyimide resin.

6. An electrophoresis apparatus comprising:
multiple capillaries to allow migration of test samples, said capillaries being arranged substantially in a plane and having an area to which an excitation light is irradiated;
a holding member for arranging at least some of said capillaries including said area substantially in said plane;
a light exciting system for irradiating said excitation light to said capillaries;
a light receiving optical system for detecting a fluorescent light from said migration of said test samples; and
a light cut-off means arranged on said capillaries, said light cut-off means being arranged to cut off light exiting said capillaries and comprising a curved surface, wherein the light cut-off means is formed within the following circumferential ranges on said capillaries:

$$\theta_1 < X < \theta_2$$

$$\pi \theta_2 < X < \pi \theta_1$$

where: $0 < \theta_1 < \theta_2 < \pi/2$
and where $\theta_1$ and $\theta_2$ are angles measured from a sequence axis running through the centers of said multiple capillaries and $\theta_1$ and $\theta_2$ are centered on a capillary rotary center axis.

7. An electrophoresis apparatus comprising:
multiple capillaries to allow migration of test samples, said capillaries being arranged substantially in a plane and having an area to which an excitation light is irradiated;
a holding member for arranging at least some of said capillaries including said area substantially in said plane;
a light exciting system for irradiating said excitation light to said capillaries;
a light receiving optical system for detecting a fluorescent light from said migration of said test samples; and
a light cut-off means arranged on said capillaries, said light cut-off means being arranged to cut off light exiting said capillaries and comprising a curved surface, further comprising a reflection means arranged on said capillaries.

8. An electrophoresis apparatus of claim 7, wherein the reflection means is formed within the following circumferential ranges on said capillaries:

$$\pi + 3 < X < 2\pi - \theta_3$$

where: $0 < \theta_3 < \pi/2$ and where $\theta_3$ is an angle measured from a sequence axis running through the centers of said multiple capillaries and $\theta_3$ is centered on a capillary rotary center axis.

9. An electrophoresis apparatus comprising:

multiple capillaries to allow migration of test samples, said capillaries having an area to which an excitation light is irradiated;

a holding member for arranging at least some of said capillaries substantially in a plane;

a light exciting system for irradiating said excitation light to said capillaries;

a light receiving optical system for detecting a fluorescent light from the migration of said test samples; and a light reflection means arranged on said capillaries and formed within the following circumferential ranges on said capillaries:

$$\pi + \theta_3 < X < 2\pi - \theta_3$$

where: $0 < \theta_3 < \pi/2$ and where $\theta_3$ is an angle measured from a sequence axis running through the centers of said multiple capillaries and $\theta_3$ is centered on a capillary rotary center axis.

10. An electrophoresis apparatus of claim 9, wherein said light reflection means are arranged on a side of said capillaries opposite to a direction in which said excitation light is emitted by said capillaries.

11. An electrophoresis apparatus of claim 9, wherein said light reflection means comprises a light reflection film.

12. An electrophoresis apparatus of claim 9, wherein said multiple capillaries include capillaries comprising a cylindrical molten quartz tube and a polyimide resin covering a portion of said molten quartz tube, and wherein said light reflection film is arranged on a portion of the molten quartz tube not covered by said polyimide resin.

13. An electrophoresis apparatus of claim 9, wherein a portion of said holding member is configured for reducing reflected light.

14. An electrophoresis apparatus of claim 9, wherein said holding member comprises a glass substrate, and wherein part of a surface of said glass substrate is frosted.

15. An electrophoresis apparatus comprising:

multiple capillaries to allow migration of test samples and said capillaries having an area to which an excitation light is irradiated;

a holding member for arranging at least some of said capillaries substantially in a plane;

a light exciting system for irradiating said excitation light to said capillaries;

a light receiving optical system for detecting a fluorescent light from the migration of said test samples;

a light cut-off means arranged on said capillaries, said light cut-off means being arranged to cut off light exiting said capillaries and comprising a curved surface; and a light reflection means arranged on said capillaries.

16. An electrophoresis apparatus of claim 15, wherein the light cut-off means comprises light cut-off film.

17. An electrophoresis apparatus of claim 15, wherein the light reflection means comprises light reflection film.

18. An electrophoresis apparatus of claim 15, wherein said multiple capillaries include capillaries comprising a cylindrical molten quartz tube and a polyimide resin covering a portion of said molten quartz tube, and wherein said light cut-off means and said light reflection means are arranged on a portion of the molten quartz tube not covered by said polyimide resin.

19. An electrophoresis apparatus of claim 15, wherein a portion of said holding member is configured for reducing reflected light.

* * * * *